(12) United States Patent
Brown et al.

(10) Patent No.: US 6,652,841 B1
(45) Date of Patent: Nov. 25, 2003

(54) ANTIPLAQUE ENZYME CONTAINING DUAL COMPONENT COMPOSITION

(75) Inventors: James R. Brown, Edison, NJ (US); Lori H. Szeles, Howell, NJ (US); Susan M. Herles, Flemington, NJ (US); Michael Prencipe, West Windsor, NJ (US); James G. Masters, Ringoes, NJ (US)

(73) Assignee: Colgate Palmolive Company, New York, NY (US)

( * ) Notice: Subject to any disclaimer, the term of this patent is extended or adjusted under 35 U.S.C. 154(b) by 0 days.

(21) Appl. No.: 10/229,622

(22) Filed: Aug. 28, 2002

(51) Int. Cl.$^7$ .............................. A61K 7/16; A61K 7/18; A61K 7/28
(52) U.S. Cl. ............................ 424/49; 424/50; 424/52
(58) Field of Search ........................ 424/49–58

(56) References Cited

U.S. PATENT DOCUMENTS

| | | | | |
|---|---|---|---|---|
| 2,946,725 A | * | 7/1960 | Norris et al. ............ | 167/93 |
| 3,105,798 A | * | 10/1963 | Holliday et al. ......... | 167/93 |
| 5,281,410 A | * | 1/1994 | Lukacovic et al. ...... | 424/52 |
| 5,780,015 A | * | 7/1998 | Fisher et al. ........... | 424/52 |
| 5,843,409 A | * | 12/1998 | Campbell et al. ....... | 424/52 |
| 5,932,192 A | * | 8/1999 | Campbell et al. ....... | 424/52 |
| 6,187,295 B1 | * | 2/2001 | Glandorf ................. | 424/52 |
| 6,350,436 B1 | * | 2/2002 | Glandorf et al. ........ | 424/52 |
| 6,379,654 B1 | * | 4/2002 | Gebreselassie et al. .. | 424/50 |
| 6,464,963 B1 | * | 10/2002 | Gambogi et al. ........ | 424/52 |

* cited by examiner

*Primary Examiner*—Shep K. Rose
(74) *Attorney, Agent, or Firm*—Bernard Lieberman

(57) ABSTRACT

A two component antiplaque dentifrice composition is disclosed which comprises first and second dentifrice components containing an enzyme such as papain and a metal salt such as stannous fluoride, the first and second dentifrice components being maintained separate from the other until dispensed for application to teeth.

18 Claims, No Drawings

ANTIPLAQUE ENZYME CONTAINING DUAL COMPONENT COMPOSITION

BACKGROUND OF THE INVENTION

1. Field of the Invention

This invention relates generally to oral compositions for enhancing oral hygiene, and more particularly, to enzyme containing dual component compositions for enhancing antiplaque efficacy of oral compositions.

2. The Prior Art

Oral compositions such as toothpastes, gels and mouth washes are designed to loosen and remove plaque in conjunction with a regular toothbrushing regimen. Dental plaque is present to some degree, in the form of a film, on virtually all dental surfaces. It is a byproduct of microbial growth, and comprises a dense microbial layer consisting of a mass of microorganisms embedded in a polysaccharide matrix. Plaque itself adheres firmly to dental surfaces and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The danger associated with the formation of plaque on the teeth lies in the tendency of plaque to build up and eventually produce gingivitis, periodontitis and other types of periodontal disease, as well as dental caries and dental calculus.

It is known to the art to incorporate antimicrobial agents such as metal salts including stannous salts such as stannous fluoride in oral compositions wherein these agents destroy or inhibit oral bacteria. Other agents are also incorporated in the oral composition to enhance the efficacy of the antimicrobial agents. For example, it is known to incorporate enzymes in oral compositions which disrupt or interfere with plaque formation and bacterial adhesion to tooth surfaces as disclosed in U.S. Pat. Nos. 2,527,686; 3,991,177; 3,194,738; 4,082,841; 4,115,546; 4,140,759; 4,152,418; 4,986,981; 5,000,939; 5,370,831; 5,431,903; 5,537,856; 5,849,271.

A problem encountered with the use of enzymes in oral care compositions is that often the enzyme of choice is not compatible with metal salts and surfactants such as anionic surfactants as these agents facilitate denaturing of the enzyme and loss of activity.

SUMMARY OF THE INVENTION

The present invention is based upon the discovery that in a dual component dentifrice comprised of separately housed dentifrice components in which the components contain an enzyme and an antibacterial metal salt normally incompatible with the enzyme, the components unexpectedly provide improved antiplaque efficacy when the components are mixed and combined during use in tooth brushing as the antiplaque activity of the enzyme and the metal salt is retained during the period of such use.

In accordance with the present invention there is provided a method for combining the plaque disruption properties of active enzymes and the plaque inhibiting properties of stannous salts using a dual component dentifrice, the dentifrice being comprised of separately housed, components containing an antibacterial metal salt such as a stannous salt and an enzyme normally incompatible with the metal salt whereupon combination of the components during use provides a superior antiplaque efficacy without significant reduction in the activity of the stannous salt or enzyme.

DESCRIPTION OF THE PREFERRED EMBODIMENTS

In the preparation of the dentifrice composition of the present invention the enzyme and antibacterial metal salt may be combined in one component or in separate components of the dual component dentifrice. The two components are preferably combined in approximately equal weight proportions, so that about one-half of the concentration of any particular ingredient within either component will be present when the components are combined and applied to the teeth, as by brushing. Both components are preferably formulated to have similar physical characteristics, so that the two components may be simultaneously delivered in the desired predetermined amounts by extrusion when separately housed in a multicompartmented tube or pump device.

FIRST DENTIFRICE COMPONENT

Enzymes

The enzymes useful in the practice of the present invention include enzymes extracted from natural fruit products such as well-known protein substances within the class of proteases, which breakdown or hydrolyze proteins. The proteolytic enzymes are obtained from natural sources or by the action of microorganisms having a nitrogen source and a carbon source. Examples of proteolylic enzymes useful in the practice of the present invention include the naturally occurring enzymes papain (from papaya), bromelain (from pineapple), as well as serine proteases such as chymotrypsin. Additional enzymes include ficin and alcalase.

Papain obtained from the milky latex of the Papaya tree is the proteolytic enzyme preferred for use in the practice of the present invention and is incorporated in the oral care composition of the present invention in an amount of about 0.1 to about 10% by weight and preferably about 0.2 to about 5% by weight, such papain having an activity of 150 to 900 units per milligram as determined by the Milk Clot Assay Test of the Biddle Sawyer Group (see J. Biol. Chem., vol. 121, pages 737–745).

Enzymes which may beneficially be used in combination with the proteolytic enzymes include carbohydrases such as glucoamylase, alpha-amylase, beta-amylase, dextranase and mutanase, tannase and lipases such as plant lipase, gastric lipase and pancreatic lipase.

Glucoamylase is a saccharifying glucoamylase of *Aspergillus niger* origin. This enzyme can hydrolyze both the alpha-D-1,6 glucosidic branch points and the alpha-1,4 glucosidic bonds of glucosyl oligosaccharides. The product of this invention comprises about 0.01 to 10% of the carbohydrases. The lipase enzyme is derived from a select strain of *Aspergillus niger*. The enzyme has maximum lipolytic activity at pH 5.0 to 7.0 when assayed with olive oil. The enzyme has 120,000 lipase units per gram. Among the carbohydrases useful in accordance with this invention are glucoamylase, alpha and beta-amylase, dextranase and mutanase.

Enzymes such as proteolytic enzymes are included in the first dentifrice component of the present invention at a concentration of about 0.05 to about 5.0% by weight and preferably about 0.2 to about 2% by weight.

Additional examples of enzymes which can be used in the practice of the present invention include other carbohydrases such as alpha-amylase, beta-amylase, dextranase and mutanase and lipases such as plant lipase, gastric lipase, pancreatic lipase, pectinase, tannase lysozyme and serine proteases.

The lipase enzyme is derived from a select strain of *Aspergillus niger*, exhibiting random cleaving of the 1,3 positions of fats and oils. The enzyme has maximum lipolytic activity at pH 5.0 to 7.0 when assayed with olive oil. The enzyme has a measured activity of 120,000 lipase units per gram. The lipase may be included in the dentifrice composition at a concentration of about 0.010 to about 5.0% by weight and preferably about 0.02 to about 0.10% by weight.

The presence of tannase enzyme can be further beneficial in facilitating the breakdown of extrinsic stain. Tannase enzymes have been purified from *Aspergillus niger* and *Aspergillus allianceus* and are useful in the hydrolysis of tannins, known to discolor the tooth surface.

Further examples of enzymes which can be used in the practice of the present invention include lysozyme, derived from egg white, which contains a single polypeptide chain crosslinked by four disulfide bonds having a molecular weight of 14,600 daltons. The enzyme can exhibit antibacterial properties by facilitating the hydrolysis of bacterial cell walls cleaving the glycosidic bond between carbon number 1 of N-acetylmuramic acid and carbon number 4 of N-acetyl-D-glucosamine, which in vivo, these two carbohydrates are polymerized to form the cell wall polysaccharide. Additionally, pectinase, an enzyme that is present in most plant species facilitates the hydrolysis of the polysaccharide pectin into sugars and galacturonic acid. Glucanase, which may be utilized to catalyze the breakdown of complex carbohydrates to glucans and the hydrolysis of beta glucan to glucose may also be used in the practice of the present invention.

Enzyme Stabilizing Agents

When enzymes are included in a dentifrice component of the present invention, ingredients which stabilize enzymes in a dentifrice environment may also be included in the component. These stabilizers protect the enzyme from inactivation by chelating metal ions which may be present in the oral composition through addition as antiplaque agents or as impurities, which metal ions have the propensity to denature the active site of the enzyme. Agents stabilizing enzymes against oxidation useful in the practice of the present invention include sodium bisulfite, metal gallates, sodium stannate, 3,5,-di-tert-butyl-4-hydroxytoluene (BHT), Vitamin E, Vitamin E acetate and ascorbic acid at concentrations between about 0.03 to about 1.5%, preferably between about 0.05 and about 0.75%.

Additional chelating agents of mono and di charged cationic species include sodium tripolyphosphate and tetrasodium pyrophosphate, ethylene diamine tetraacetic acid and sodium gluconate and may be incorporated in the dentifrice component at a concentration of about 0.01 to about 1% by weight and preferably between about 0.1 to about 0.5% by weight.

Certain antibacterial metal salts, such as stannous ion releasable salts have unexpectedly been found to be compatible with enzymes and therefore may be incorporated in the first dentifrice component containing enzymes, when metal ion stabilizing agents of the type disclosed above are present in the dentifrice component.

Antibacterial Metal Salts

The first dentifrice component of the present invention is generally comprised of about 0.1 to about 5.0% and preferably about 0.5 to about 3% by weight of an antibacterial metal salt including water soluble salts such as zinc citrate, zinc gluconate, copper sulfate and particularly stannous ion releasing salts such as stannous fluoride, stannous chloride, stannous phosphate, stannous citrate and stannous gluconate. Stannous fluoride is the preferred stannous salt. In the preparation of dentifrices containing stannous salts such as SnF2, the dentifrice contains about 0.30 to about 1.5% by weight SnF2 and preferably 0.4 to 1.3% by weight. Additional stannous salts such as stannous chloride may also be added to improve the stability of the stannous fluoride salts. The stannous chloride is included in the dentifrice component at a concentration in the range of 0.3 to about 1.5% by weight and preferably about 0.3 to about 1.0% by weight.

Metal Stabilizing Agents

Polycarboxylic food grade organic acid compounds may be incorporated in the first dentifrice component to stabilize antibacterial metal salts such as stannous salts to oxidation to insoluble stannic and inactive ions, as disclosed in U.S. Pat. No. 5,578,293, herein incorporated by reference.

The term "organic acid compound" includes within its meaning the free acid or its water soluble salt and is incorporated in the first dentifrice component in the range of from about 0.01 to about 10% by weight and preferably from about 0.5 to about 5% by weight.

Suitable organic acid compounds useful in the practice of the present invention include polycarboxylic food grade organic acids such as citric acid, lactic acid, tartaric acid, gluconic acid, succinic acid, malic acid, fumaric acid and their water soluble salts such as the alkali metal salts including sodium or potassium citrate and sodium or potassium lactate.

Dentifrice Vehicle

Orally-acceptable vehicles used to prepare the first as well as the second dentifrice component of the present invention include a water-phase, containing a humectant therein. The humectant is preferably glycerin, sorbitol, xylitol, and/or propylene glycol of molecular weight in the range of 200 to 1,000; but, other humectants and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 25 to 70% by weight of the dentifrice component. Water employed in the preparation of commercially suitable oral compositions should preferably be deionized and free of organic impurities. These amounts of water include the free water which is added plus that which is introduced with other materials such as with sorbitol.

Nonionic Surfactants

Concentrations of ionic surfactants conventionally used in the preparation of dentifrice compositions are not fully compatible with certain classes and types of enzymes. To prepare the enzyme containing first component of the dentifrice composition of the present invention, nonionic surfactants compatible with enzymes are preferably used to prepare the first dentifrice component when an enzyme is combined with an antibacterial metal salt such as a stannous salt, in the dentifrice component. Examples of suitable nonionic surfactants include nonanionic polyoxyethylene surfactants such as Polyoxamer 407, Steareth 30, Polysorbate 20, and PEG-40 castor oil (oxyethylated hydrogenated castor oil) and amphoteric surfactants such as cocamiopropyl betaine (tegobaine) and cocamidopropyl betaine lauryl glucoside condensation products of ethylene oxide with various hydrogen containing compounds that are reactive therewith and have long hydorphobic chains (e.g., aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides and other fatty moieties, and with propylene oxide and polypropylene oxides, for example, Pluronic®materials, e.g., Pluronic 127. Preferred surfactants include a concentration in the dentifrice composition of between about 2 to about 10% by weight and preferably between about 3.5 to 6.5% by weight. When enzymes are not present in the first dentifrice component, ionic surfactants of the type and concentration as hereinafter described may be used to prepare the first dentifrice component.

Abrasives

In the preparation of dentifrice components of the present invention abrasives which may be used to prepare both dentifrice components of the dual component dentifrice of the present invention include silica abrasives such as precipitated silicas having a mean particle size of up to about 20 microns, such as Zeodent 115, marketed by J.M. Huber Chemicals Division, Havre de Grace, Md. 21078, or Sylodent 783 marketed by Davison Chemical Division of W.R. Grace & Company. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

Preferred abrasive materials useful in the practice of the preparation of the dentifrice components in accordance with the present invention include silica gels and precipitated amorphous silica having an oil absorption value of less than 100 cc/100 g silica and preferably in the range of from about 45 cc/100 g to less than about 70 cc/100 g silica. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Oil absorption values are measured using the ASTM Rub-Out Method D281. The low oil absorption silica abrasive is present in the dentifrice compositions of the present invention at a concentration of about 5 to about 40% by weight and preferably about 10 to about 30% by weight.

Low oil absorption silica abrasives particularly useful in the practice of the present invention are marketed under the trade designation Sylodent XWA by Davison Chemical Division of W.R. Grace & Co., Baltimore, Md. 21203. Sylodent 650 XWA. This silica abrasive is a silica hydrogel composed of particles of colloidal silica having a water content of 29% by weight averaging from about 7 to about 10 microns in diameter and an oil absorption of less than 70 cc/100 g of silica and is a preferred example of a low oil absorption silica abrasive useful in the practice of the present invention.

The dentifrice components of the present invention can contain a variety of optional ingredients. As described below, such optional ingredients can include, but are not limited to, thickening agents, a source of fluoride ions, a flavoring agent, antitartar and coloring agents.

Thickening Agents

Thickening agents used in the preparation of the dentifrice components of the present invention include natural and synthetic gums and colloids. Not all naturally occurring polymer thickeners (such as cellulose or carrageenans) are compatible with enzymes. Thickeners compatible with enzymes such as proteolytic enzymes, include xanthan gum, polyglycols of varying molecular weights sold under the tradename Polyox and polyethylene glycol. Compatible inorganic thickeners include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J.M. Huber Chemicals Division, Havre de Grace, Md. 21078; and Sylodent 15, available from Davison Chemical Division of W.R. Grace Corporation, Baltimore, Md. 21203. Other inorganic thickeners include natural and synthetic clays, lithium magnesium silicate (Laponite) and magnesium aluminum silicate (Veegum).

The thickening agent is present in the dentifrice composition in amounts of about 0.1 to about 10% by weight, preferably about 0.5 to about 4.0% by weight.

Fluoride and Other Active Agents

The oral composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts. For example, preferred fluoride sources which are compatible with enzymes present in the composition are sodium fluoride, potassium fluoride, sodium fluorosilicate, sodium monfluorophosphate (MFP), ammonium fluorosilicate, as well as tin fluorides, such as stannous fluoride and stannous chloride. Sodium fluoride or MFP is preferred.

In addition to fluoride compounds, there may also be included in the oral compositions of the present inventions antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$, polyphosphates such as sodium tripolyphosphate, sodium hexametaphosphate and cyclic phosphates such as sodium tripolyphosphate sodium trimetaphosphate. These antitartar agents are included in the dentifrice composition at a concentration of about 1 to about 5% by weight.

Another active agent useful in dentifrice compositions of the present invention are antibacterial agents, which can be from 0.2 to 1.0% by weight of the dentifrice composition. Such useful antibacterial agents include non-cationic antibacterial agents which are based on phenolic or bisphenolic compounds, such as halogenated diphenyl ethers such as Triclosan (2,4,4'-trichloro-2'-hydroxydiphenyl ether).

Flavor

The dentifrice components of the present invention may also contain a flavoring agent. Flavoring agents which are used in the practice of the present invention include essential oils as well as various flavoring aldehydes, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are oils of peppermint and spearmint.

The flavoring agent is incorporated in the oral composition at a concentration of about 0.1 to about 5% by weight and preferably about 0.5 to about 1.5% by weight.

Other Ingredients

Various other materials may be incorporated in this component of the dual component dentifrice, includes desensitizers, such as potassium nitrate; whitening agents, such as hydrogen peroxide, calcium peroxide and urea peroxide; preservatives; silicones; and chlorophyll compounds. These additives, when present, are incorporated in the dentifrice components of the present invention in amounts which do not substantially adversely affect the properties and characteristics desired.

SECOND DENTIFRICE COMPONENT

The vehicle of the second dentifrice component is formulated to have a composition similar to the vehicle of the first dentifrice component, so that two components will be of substantially equivalent rheologies, which will permit them to be synchronously coextrudable from a container in which the components are separately housed. In order to maintain that the physical characteristics of the second component have rheological properties substantially equivalent to the first component, the vehicle composition of the second component, specifically the humectant and abrasive content, is adjusted.

The water and humectant comprise the liquid portion of the second dentifrice component. The humectant is preferably sorbitol, but other humectants such as glycerin and polyethylene glycol may also be employed. The humectant content is generally in the range of about 30% to about 70% by weight and preferably about 40 to about 65% by weight the water content is in the range of about 5 to about 40% by weight and preferably 10 to about 30% by weight.

Preferred abrasives are siliceous materials, such as silica, and preferably a precipitated amorphous hydrated silica, and preferably a precipitated amorphous hydrated silica, such as Zeodent 115, available from Huber Corporation. The abrasive is generally present in the second dentifrice component at a concentration of about 10 to about 40% by weight and preferably about 15 to about 30% by weight.

Ionic Surfactants

As nonionic surfactants have relatively limited foaming properties, an anionic surfactant which provides the dentifrice composition, upon mixing of the dentifrice components, with superior foaming properties, is incorporated in the second dentifrice component in which the incompatible enzyme is absent. Examples of preferred anionic surfactants include higher alkyl sulfates such as potassium or sodium lauryl sulfate which is preferred, higher fatty acid monoglyceride monosulfates, such as the salt of the monosulfatedmonoglyceride of hydrogenated coconut oil fatty acids, alkyl aryl sulfoantes such as sodium dodecyl benzene sulfonate, higher fatty sulfoacetates, higher fatty acid esters of dihydorxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine and the salts of N-lauroyl, N-myristoyl, or N-palmitoyl sarcosine.

The anionic surfactant is generally present in the second dentifrice component of the present invention at a concentration of about 0.5 to about 10.0% by weight and preferably about 2 to abut 7% by weight. In the event that an enzyme is included in the second dentifrice component, a compatible nonionic surfactant as hereinbefore described is used in place of the ionic surfactant.

Thickening Agent

A thickening agent may be incorporated in the second dentifrice component at a concentration of about 0.5 to abut 10% by weight and preferably about 1 to about 5% by weight. Organic thickeners of natural and synthetic gums of the same type used to prepare the first dentifrice component may also be incorporated at a concentration of about 0.1 to abut 3% by weight and preferably about 0.2 to about 2% by weight.

Additional ingredients such as fluoride and other active agents such as antitartar agents, flavors and sweeteners similar to that used for the preparation of the first dentifrice component may be included in the preparation of the second dentifrice component at similar concentrations.

Anionic carboxylate polymers as disclosed in U.S. Pat. Nos. 5,188,821 and 5,192,531 may be incorporated in the second dentifrice component when enzymes are not present in the component, to enhance the efficacy of antitartar agents such as sodium pyrophosphate. Examples of such polymers include synthetic anionic polymeric polycarboxylates in the form 1:4 to 4:1 copolymers of maleic anhydride or acid with another polymerizable ethylenically unsaturated monomer, preferably methyl vinyl ether/maleic anhydride having a molecular weight (M.V.) of about 30,000 to about 1,000,000, most preferably about 30,000 to about 800,000. these copolymers are available for example as Gantrez, e.g., AN139 (M.W. 500,000), AN 119 (M.W. 250,000) and preferably S-97 Pharmaceutical Grade (M.W. 700,000) available from ISP Technologies, Inc., Bound Brook, N.J. 08805.

Preparation of Dentifrice Components

To prepare an antibacterial metal salt/enzyme containing dentifrice component of the present invention, generally the humectants such as glycerin, sorbitol are dispersed in the water in a conventional mixer under agitation. Into the dispersion are added antibacterial metal salts, such as stannous fluoride, stannous chloride, stannous salt stabilizing agents such as trisodium citrate and citric acid, antitartar agents such as tetrasodium pyrophosphate and any sweeteners; the resultant mixture is agitated until a homogeneous gel phase is formed. Into the gel phase is added a pigment such as $TiO_2$. These ingredients are mixed until a homogenous phase is obtained. Thereafter a dispersion in water and humectant of enzyme compounds such as papain, glycoamylase is added and admixed with the homogeneous phase This mixture is then transferred to a high speed/vacuum mixer; wherein, thickeners such as xanthan gum, Zeodent 165, iota carrageenan are added to the mixture. Thereafter the abrasive is added together with the flavor oils to be included in the composition and the solution is added along with the nonionic surfactants to the mixture, which is then mixed at high speed for from 5 to 30 minutes, under vacuum of from about 20 to 50 mm of Hg, preferably about 30 mm Hg. The resultant product is in each case is a homogeneous, semi-solid, extrudable paste or gel product.

To prepare the second dentifrice component of the present invention, generally the humectants, for example, sorbitol are dispersed with any organic thickeners and sweetener. Water is then added into this dispersion and the ingredients mixed until a homogenous phase is obtained for the component. Thereafter silica abrasive, ionic surfactant anionic carboxylate, thickening agents and flavor ingredients are added and the ingredients mixed at high speed under vacuum of from about 20 to 100 mm of Hg. The resultant product, in the case of each component, is a homogeneous, semi-solid, extrudible paste product.

The dual component dentifrice composition of the present invention is packaged in a suitable dispensing container in which the components are maintained physically separated and from which the separated components may be dispensed synchronously as a combined ribbon for application to a toothbrush. Such containers are known in the art. An example of such a container is a two compartment dispensing container, such as a pump or a tube, having collapsible sidewalls, as disclosed in U.S. Pat. Nos. 4,487,757 and 4,687,663; wherein, the tube body is formed from a collapsible plastic web such as polyethylene or polypropylene and is provided with a partition within the container body defining separate compartments in which the physically separated components are stored and from which they are dispensed through a suitable dispensing outlet.

The following example is further illustrative of the present invention, but it is understood that the invention is not limited thereto. All amounts and proportions referred to herein and in the appended claims are by weight, unless otherwise stated.

EXAMPLE

A two component (Component A and B) antibacterial stannous salt/enzyme containing dentifrice of the present invention designated "Composition X" was prepared, wherein Component A was prepared containing a combination of stannous salts and the enzymes papain and glycoamylase and the second Component B was prepared having incorporated therein the anionic surfactant, sodium lauryl sulfate. No stannous salts or enzymes were present in Component B. The ingredients of Components A and B are listed in Table I below.

TABLE I

| | Composition X | |
|---|---|---|
| Ingredient | Component A (Wt. %) | Component B (Wt. %) |
| Water | 17.00 | 7.0 |
| Citric acid | 0.531 | — |
| Trisodium citrate | 2.65 | — |
| Stannous fluoride | 0.908 | — |
| Stannous chloride | 0.60 | — |
| Glycerine | 40.29 | 12.0 |
| Carboxymethyl cellulose | 0.80 | 0.80 |
| Xanthan gum | 0.50 | — |
| Sodium saccharin | 0.40 | 0.45 |
| Tetrasodium pyrophosphate | 0.50 | 1.00 |
| Pluronic F127 | 2.00 | — |
| Titanium dioxide | 0.50 | — |
| PEG-40 castor oil | 6.00 | — |
| Zeodent 165 | 5.50 | 3.00 |
| Sylodent XWA 650 | 20.0 | 10.0 |
| Zeodent 115 | — | 1.20 |
| Flavor | 1.20 | — |
| Papain | 0.412 | — |
| Glucoamylase | 0.200 | — |
| Sodium tripolyphosphate | — | 7.00 |
| Sorbitol | — | 27.21 |
| Sodium hydroxide - 50% soln | — | 2.00 |
| Iota carrageenan | — | 0.35 |
| Sylodent 783 | — | 11.0 |
| Sodium lauryl sulfate (30% soln.) | — | 9.31 |
| Gantrez S-97 | — | 7.69 |

A second two component (Component C and D) dentifrice designated "Composition Y" was prepared having ingredients similar to Composition X except that no enzyme was present in the first stannous salt containing component (Component C), the enzymes papain and glucoamylase being present in the second component (Component D). The ingredients of Components C and D are listed in Table II below.

TABLE II

| | Composition Y | |
|---|---|---|
| Ingredient | Component C (Wt. %) | Component D (Wt. %) |
| Water | 21.45 | 16.00 |
| Citric acid | 0.531 | — |
| Trisodium citrate | 2.65 | 0.908 |
| Stannous fluoride | 0.60 | — |
| Stannous chloride | 29.55 | — |
| Glycerine | 0.80 | 20.00 |
| Carboxymethyl cellulose | 0.50 | 0.65 |
| Xanthan gum | 0.40 | 0.55 |
| Sodium saccharin | 0.50 | 0.40 |
| Tetrasodium pyrophosphate | 2.00 | 2.00 |
| Pluronic F-127 | 0.50 | 1.50 |
| Titanium dioxide | 6.00 | 0.40 |
| PEG-40 castor oil | 4.50 | — |
| Zeodent 165 | 10.00 | 2.00 |
| Sylodent XWA 650 | 11.00 | 20.00 |
| Zeodent 115 | 1.20 | 5.00 |
| Flavor | — | 1.20 |
| Papain | — | 0.412 |
| Glucoamylase | — | 0.20 |
| Sodium tripolyphosphate | — | 3.00 |
| Sorbitol | — | 19.258 |
| Sodium lauryl sulfate (30% soln.) | 6.90 | — |
| $NaH_2PO_4$ | — | 0.03 |
| $NaHPO_4$ | — | 0.20 |
| Sodium bisulfite | — | 0.10 |
| Polysorbate 20 | — | 2.00 |
| Tego betaine ZP | — | 2.00 |
| PEG-600 | — | 3.00 |
| Polyox | — | 0.10 |

For purposes of comparison, a dual component dentifrice composition designated "Composition Z" was prepared having components E and F in which stannous salts were present in the composition but no enzymes. The ingredients of Components E and F are listed in Table III below.

TABLE III

| | Composition Z | |
|---|---|---|
| Ingredient | Component E (Wt. %) | Component F (Wt. %) |
| Water | 21.45 | 12.30 |
| Citric Acid | 0.531 | — |
| Trisodium citrate | 2.65 | — |
| Stannous fluoride | 0.908 | — |
| Stannous chloride | 0.60 | — |
| Glycerine | 31.45 | 12.0 |
| Carboxymethyl cellulose | 0.80 | 0.80 |
| Xanthan gum | 0.50 | 0.35 |
| Sodium saccharin | 0.40 | 0.45 |
| Tetrasodium pyrophosphate | 0.50 | 1.00 |
| Pluronic F-127 | 2.0 | — |
| Titanium dioxide | 0.50 | — |
| PEG-40 castor oil | 6.0 | — |
| Zeodent 165 | 4.5 | 3.00 |
| Sylodent XWA 650 | 10.0 | 10.0 |
| Zeodent 115 | 11.0 | — |
| Flavor | 1.20 | 1.20 |
| Sodium tripolyphosphate | — | 7.0 |
| Sorbitol | — | 27.21 |
| Sylodent 783 | — | 11.0 |
| Gantrez S-97 | — | 7.69 |
| Sodium Hydroxide 50% Soln. | — | 2.0 |
| Sodium lauryl sulfate (30% soln.) | 5.0 | 4.0 |

The antibacterial efficacy of Compositions X and Y was evaluated using A. viscous as the test bacteria. The evaluation was performed using whole human saliva, applied to eight hydroxyapatite (HAP) disks to form a pellicle. After 45 minutes of pellicle formation, media flow is started and the plaque forming bacteria is pumped across the disks. Then the saliva, together with bacteria media composed of proteose peptone, trypticase peptone, potassium chloride, cysteine hydrochloride, yeast extract, and dextrose, is continuously pumped through the chamber at the rate of 1 ml/min. After four hours a 10 mL treatment slurry of Compositions X and Y diluted with water at 1:2 ratio is applied across the HAP disk, after which the saliva flow, at 1 l/min., is resumed for 10 minutes to wash out residual slurry. After six hours the same procedure (involving a 30-second Composition X or Y slurry treatment) is repeated for a total of four treatments over three days. After 72 hours the resulting HAP disks are removed and added to 2 mL of 0.025% Trypsin solution and incubated for 45 minutes. The disks are then removed and the solution is sonicated for three seconds. The bacterial growth into the HAP disks is measured as turbidity or optical density of the Trypsin solution at an absorbance at 610 nm using a spectrophotometer. Optical density measurements indicate the degree of bacterial growth on the plates, that is, the lower the optical density, the greater the antiplaque efficacy of the dentifrice slurry being tested.

For purposes of comparison the procedure of the Example was repeated using comparative Composition Z. The results of the evaluation of Compositions X, Y, Z are recorded in the Table IV below.

TABLE IV

| BACTERIAL GROWTH REDUCTION | | | |
|---|---|---|---|
| Composition | X | Y | Z |
| Mean Optical Density Reading | 0.03 | 0.10 | 0.16 |
| % Reduction v. Composition Z | 81% | 38% | — |

The results recorded in Table IV above clearly indicate that combining enzymes with a stannous salt such as SnF2 provides a significant and unexpected improvement in antiplaque efficacy/bacterial reduction when compared to a stannous salt containing oral compositions in which enzymes are not present. It is hypothesized from the data recorded in Table IV that enzymes facilitate the breaking down of the plaque ultrastructure and matrix to provide a more efficient delivery pathway for antibacterial agents like stannous fluoride.

What is claimed is:

1. A dual component dentifrice composition having superior antibacterial efficacy which comprises first and second dentifrice components which contain an enzyme and an antibacterial metal salt in separate orally acceptable dentifrice vehicles, and in which an anionic surfactant is present solely in the dentifrice vehicle containing the metal salt, the first and second components being maintained separate from each other until dispensed and combined for application to teeth whereby heightened antibacterial efficacy against plaque causing oral bacteria is obtained.

2. The composition of claim 1 wherein the enzyme is papain.

3. The composition of claim 1 wherein the enzyme is glucoamylase.

4. The composition of claim 1 wherein the antibacterial metal salt is a stannous salt.

5. The composition of claim 1 wherein the antibacterial metal salt is $SnF_2$.

6. The composition of claim 4 wherein the stannous salt is a combination of $SnF_2$ and $SnCl_2$.

7. The composition of claim 1 wherein the enzyme is present in the composition at a concentration of about 0.05 to about 5% by weight.

8. The composition of claim 1 wherein the antibacterial metal salt is present in the composition at a concentration of about 1 to about 5% by weight.

9. A method for improving the antibacterial efficacy of an oral care composition comprising preparing first and second dentifrice components containing an enzyme and an antibacterial metal salt in separate orally acceptable vehicles, and in which an anionic surfactant is present solely in the dentifrice vehicle containing the metal salt, separately housing the first and second components, dispensing the first and second components simultaneously, combining the dispensed components and thereafter applying the combined components to the teeth whereby heightened antibacterial efficacy against plaque causing oral bacteria is obtained.

10. The method of claim 9 wherein the enzyme is papain.

11. The method of claim 9 wherein the enzyme is glucoamylase.

12. The method of claim 9 wherein the antibacterial metal salt is a stannous salt.

13. The method of claim 12 wherein the antibacterial stannous salt is $SnF_2$.

14. The method of claim 13 wherein the antibacterial stannous salt is a combination of $SnF_2$ and $SnCl_2$.

15. The method of claim 9 wherein the antibacterial stannous salt is present in the composition at a concentration of about 1 to abut 5% by weight.

16. The method of claim 9 wherein the enzyme is present in the composition at a concentration of about 0.05 to about 5% by weight.

17. The method of claim 9 wherein the stannous salt is present in the composition at a concentration of about 1 to about 5% by weight.

18. The method of claim 9 wherein the first and second components are housed in a common container and are separated from one another by a wall integrally formed with the container which prevents mixing of the components prior to being dispensed.

* * * * *